US00PP25762P3

(12) United States Plant Patent
Madsen

(10) Patent No.: US PP25,762 P3
(45) Date of Patent: Jul. 28, 2015

(54) ***CAMPANULA* PLANT NAMED 'PKMFORMA04'**

(50) Latin Name: *Campanula formanekiana*
Varietal Denomination: PKMForma04

(71) Applicant: Gartneriet PKM A/S, Odense N (DK)

(72) Inventor: Christian Hald Madsen, Korsor (DK)

(73) Assignee: Gartneriet PKM A/S, Odense N (DK)

( * ) Notice: Subject to any disclaimer, the term of this patent is extended or adjusted under 35 U.S.C. 154(b) by 182 days.

(21) Appl. No.: 13/987,008

(22) Filed: Jun. 25, 2013

(65) Prior Publication Data

US 2014/0380542 P1 Dec. 25, 2014

(51) Int. Cl.
*A01H 5/00* (2006.01)

(52) U.S. Cl.
USPC ..... Plt./414

(58) Field of Classification Search
USPC ..... Plt./414
See application file for complete search history.

(56) References Cited

PUBLICATIONS

Printout of application information from Community Plant Variety Office (CPVO) website for corresponding CPVO application No. 2013/1163 filed Apr. 23, 2013 (1 page) (http://www.cpvoextranetcpvo.europa.eu).

*Primary Examiner* — Susan McCormick Ewoldt
(74) *Attorney, Agent, or Firm* — Foley & Lardner LLP

(57) ABSTRACT

A new and distinct cultivar of *Campanula* plant named 'PKMFORMA04', characterized by its large, campanulate flowers, pyramidal growth habit, and silvery green foliage.

4 Drawing Sheets

Latin name of genus and species of the plant claimed: *Campanula formanekiana.*

Variety denomination: 'PKMForma04'.

BACKGROUND OF THE INVENTION

The present invention relates to a new and distinct cultivar of *Campanula* plant, botanically known as *Campanula formanekiana,* commonly known as Bellflower, and hereinafter referred to by the name 'PKMForma04'.

The new *Campanula, 'PKMForma*04', is a product of a planned breeding program conducted by the inventor, Christian Hald Madsen, in Søhus, Denmark.

The new *Campanula* cultivar originated from a cross made in a controlled breeding program by the inventor in 2009 in Søhus, Denmark. The female or seed parent is an unpatented, proprietary *Campanula formanekiana* cultivar. The male or pollen parent is an unpatented, proprietary *Campanula formanekiana* cultivar. The new *Campanula* 'PKMForma04' was discovered and selected by the inventor as a single flowering plant within the progeny of the stated cross in 2008 in a controlled environment in Søhus, Denmark.

Asexual reproduction of the new *Campanula* cultivar by terminal cuttings was first performed in 2009 in Søhus, Denmark, and has demonstrated that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be the unique characteristics of 'PKMForma04'. These characteristics in combination distinguish 'PKMForma04' as a new and distinct cultivar:

1. Pyramidal growth form;
2. Large, campanulate violet (RHS NN88B) flowers with basal part and veins of brighter color (RHS 92D).

Side-by-side comparisons were conducted by the inventor in Søhus, Denmark between plants of the new *Campanula formanekiana* 'PKMForma04' and the comparison variety *Campanula formanekiana* 'PKMfor168' (patented, U.S. Plant Pat. No. 19,812; CPVO grant no. 27693). Plants of 'PKMForma04' and of 'PKMfor168' differ in the following characteristics:

1. Plants of 'PKMForma04' have darker violet flowers than plants of PKMfor168;
2. Plants of 'PKMForma04' have a larger colored part of the flowers than PKMfor168;
3. Plants of 'PKMForma04' need no pinching of laterals to produce quality pot plants, as do plants of 'PKMfor168'.

Data on the plants of the parent varieties are no longer available for comparison with plants of the new cultivar *Campanula formanekiana* 'PKMForma04'.

BRIEF DESCRIPTION OF THE PHOTOGRAPHS

The accompanying colored photographs illustrate the overall appearance of the new *Campanula* 'PKMForma04', showing the colors as true as it is reasonably possible to obtain in colored reproductions of this type. Colors in the photographs may differ slightly from the color values cited in the detailed botanical description, which more accurately describe the actual colors of 'PKMForma04'.

DETAILED BOTANICAL DESCRIPTION

Figure 1:
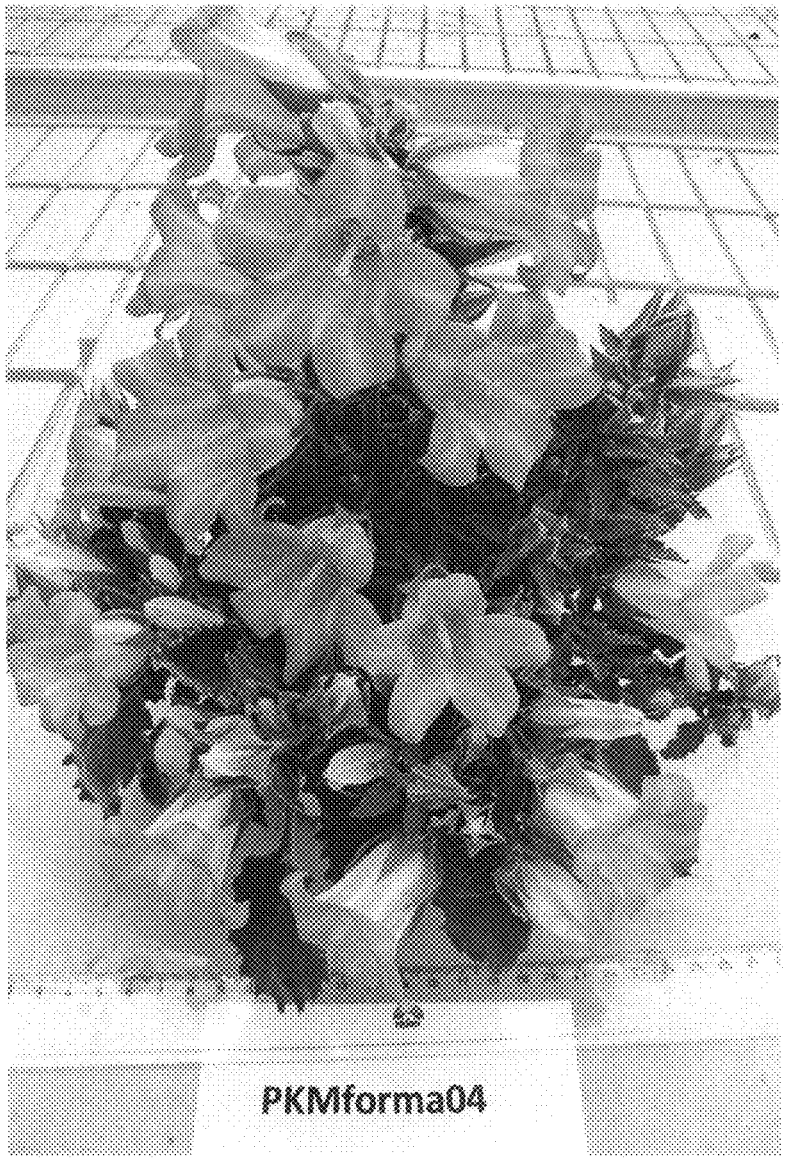
FIG. 1 shows a side perspective view of a typical flowering plant of 'PKMForma04'.
Figure 2:
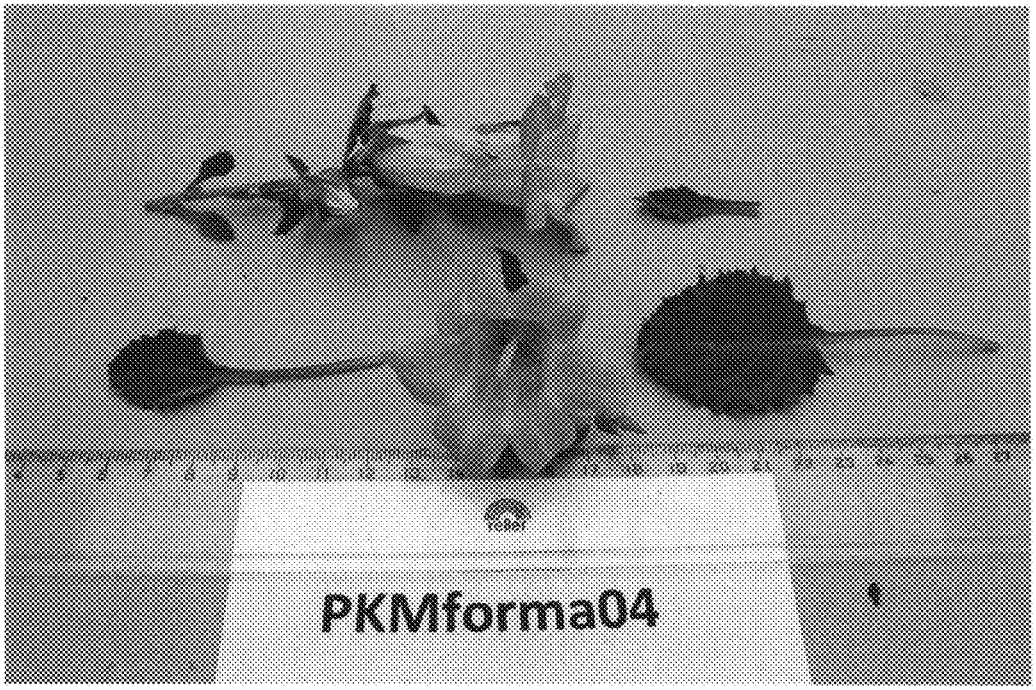
FIG. 2 shows a close-up view of a typical lateral branch of a typical inflorescence and individual leaves of a plant of 'PKMForma04'.
Figure 3:
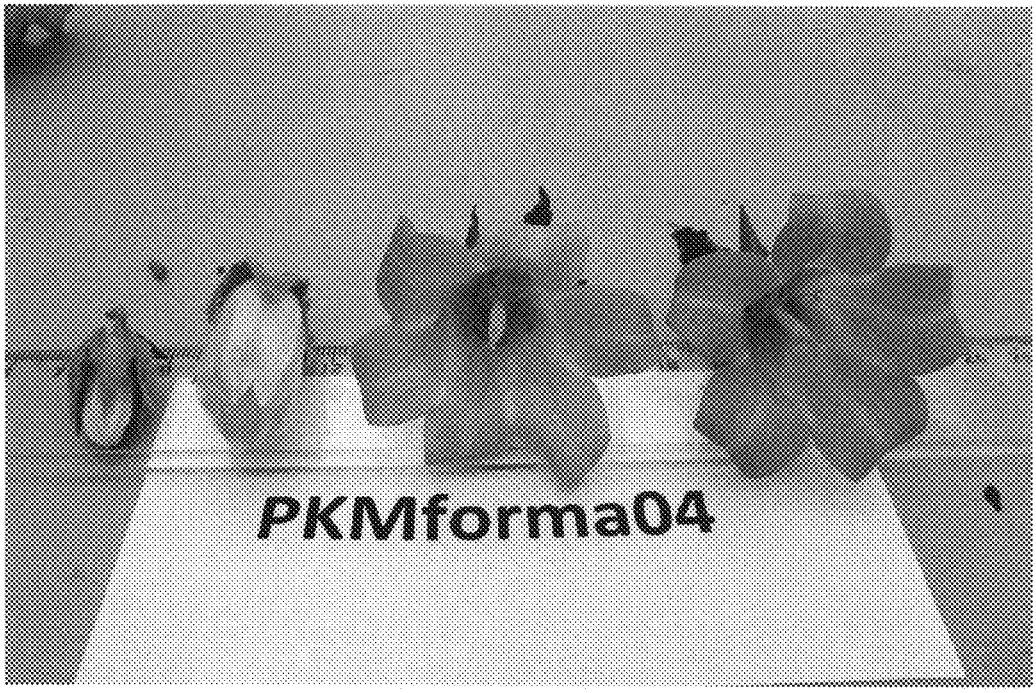
FIG. 3 shows a close-up view of different stages of development of a typical flower of 'PKMForma04', from bud to fully-opened flower.
Figure 4:
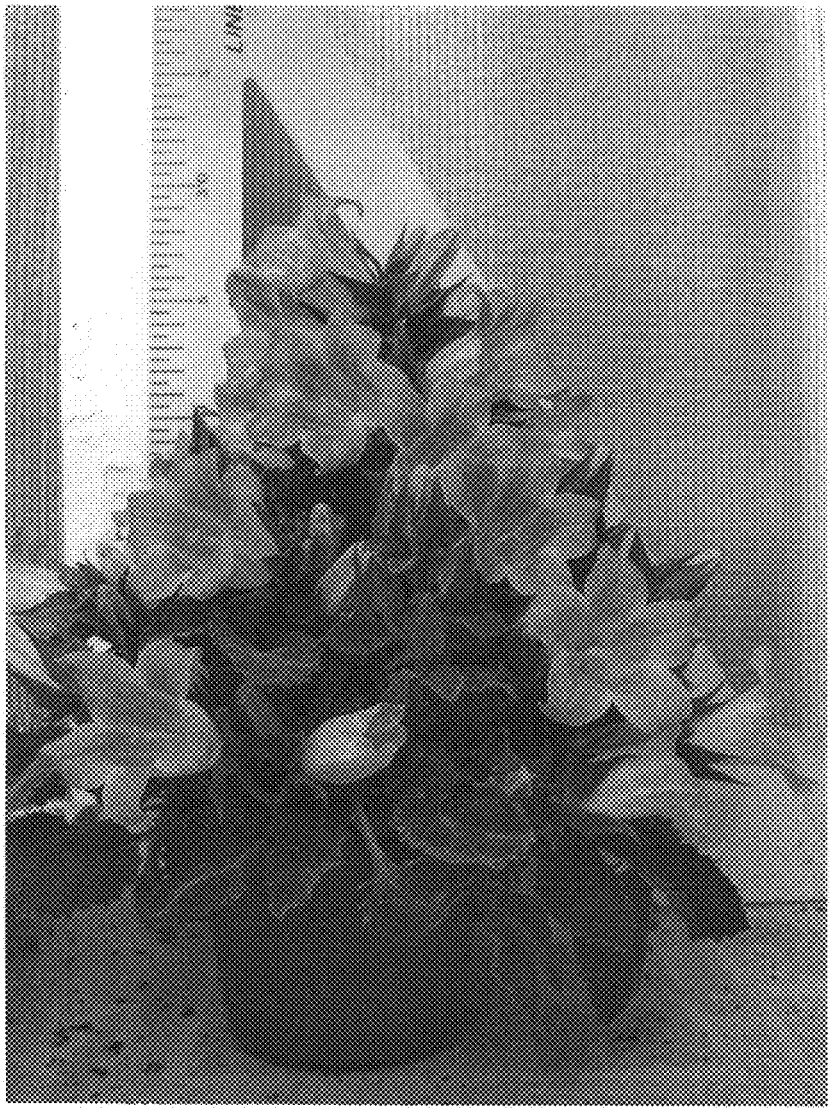
FIG. 4 shows a close-up side view of a typical flowering plant of the comparison variety 'PKMfor168' (comparisons should consider that the photograph in FIG. 3 was not taken at the same time of year as FIG. 1).

The new *Campanula* 'PKMForma04' has not been observed under all possible environmental conditions. The phenotype of the new cultivar may vary significantly with variations in environment such as temperature, light intensity, day length, and fertility level without any variance in genotype.

The aforementioned photographs, together with the following observations, measurements and values describe plants of the new *Campanula* 'PKMForma04' as grown in a heated and lighted, glass-covered greenhouse in Søhus, Denmark, under conditions which closely approximate those generally used in commercial practice where day temperatures in the greenhouse range from 18-22° C. and the night temperature averages about 16° C. Ambient light levels used while growing plants of 'PKMForma04' are +100 W/m$^2$. Plants of 'PKMForma04' are grown with long day photoperiodic treatments and propagation and seedlings are exposed to 10 hour short photoperiodic treatments. No growth retardants are used.

The age of the 'PKMForma04' plants described is 14 weeks old and grown in 11 cm pots. Color references are made to The Royal Horticultural Society Colour Chart (R.H.S.), 5$^{th}$ edition, except where general colors of ordinary significance are used.

Classification:

*Botanical.*—*Campanula formanekiana.*

*Variety denomination.*—PKMForma04.

Parentage:

*Female or seed parent.*—Unpatented, proprietary *Campanula formanekiana* cultivar.

*Male or pollen parent.*—Unpatented, proprietary *Campanula formanekiana* cultivar.

Propagation:

*Type cutting.*—Terminal vegetative cuttings.

*Time to initiate roots.*—About 10 to 14 days at 18 to 21° C. in tunnels in a greenhouse.

*Root description.*—Fine, well branched. Fibrous root structures.

Plant description:

*Form.*—Biennial plant with overall pyramidal plant shape. Campanulate flowers in racemes.

*Crop time.*—After rooting, about 18 weeks are required to produce finished flowering plants in 11 cm pots.

*Vigor.*—Good.

*Plant height* (*from pot rim to top of plant plane*).—About 20 to 25 cm.

*Plant spread* (*width*).—25-30 cm.

*Branching habit.*—After bolting, main stem forms lateral branches/flowers from all leaf axils. No pinching required. General: Plant contains/produces a pale orange latex (RHS 23D).

*Lateral branches.*—Quantity: About 20-30 per plant. Leaves per Lateral Branch: 2-8 (reduced with increasing stem height, giving the pyramidal growth habit). Length (including flowers): 11 cm to 14 cm. Diameter: 1 mm to 2 mm. Internode Length: 5 to 15 mm.

*Stem.*—Shape: Round with small wings. Strength: Strong. Aspect: Stiff. Pubescence: Present. Color: RHS 137D, green.

Foliage description:

*Basal leaves.*—Arrangement: Single, rosulate. Overall shape: Ovate to orbicular. Apex shape: Obtuse to rounded. Base shape: Orbicular to cordate. Length: 40-50 mm. Width: 35-40 mm. Margin: Dentate to Serrate, more prominent on basal leaves than on apical leaves. Texture (both sides): Stiff, Pubescent. Pubescence: Canescent, both sides.

*Apical* (*stem*) *leaves.*—Arrangement: Single, alternate. Overall shape: Elliptic. Apex shape: Acute. Base shape: Acute to Obtuse. Length: About 10 to 30 mm (length decreases with increasing stem height). Width: About 3 to 20 mm (width decreases with increasing stem height). Margin: Dentate to Serrate, more prominent on basal leaves than on apical leaves. Texture (both sides): Stiff, pubescent. Pubescence: Canescent, both sides.

*Basal & apical leaves.*—Foliage Color: Mature: Upper Surface: Yellow-Green, Between RHS 146A and RHS 147B. Lower Surface: Yellow-Green, Between RHS 146A and RHS 147B.

*Venation.*—Pattern: Pinnipalmate. Color: Upper Surface: Slightly paler than leaf blade, but less pronounced than on lower surface, RHS 138C, green. Lower Surface: Slightly paler than leaf blade, RHS 138C, green.

*Petiole.*—Length: Basal Leaves: 40 to 60 mm. Apical (Stem) Leaves: 10 to 20 mm. Diameter: Basal Leaves: 0 mm to 2 mm. Apical (Stem) Leaves: 0 mm to 2 mm. Color: Slightly paler than leaf blade (as for venation), RHS 138C, green. Durability to Stresses: Good.

Inflorescence description:

*Flower arrangement and shape.*—Single, large, campanulate flowers in raceme with outward aspect and reflexed petal tips. Lower lateral branches develop individual racemes.

*Natural flowering season.*—Spring to Early Summer. Season can be extended by short and long day treatments.

*Time to flower.*—About 8-10 weeks of long days.

*Flower longevity.*—On the plant, flowers last about 7 to 11 days; however, longevity of individual flowers is highly dependent on temperature and light conditions. Flowers persistent.

*Fragrance.*—Present. Mild and sweet floral.

*Inflorescence size.*—Height: 15 to 20 cm. Diameter: 10-14 cm.

*Number of flowers per lateral stem.*—1 to 10, lower lateral branches have the most flowers.

*Number of flowers and buds per plant.*—About 100 to 200, depending on developmental stage.

*Buds.*—Length: Up to 30 mm. Diameter: Up to 15 mm. Shape: Oblong, petals forming a ribbed tube. Color: Changing from RHS 1D, green-yellow to almost the color of the flower, RHS N88B violet at the tip.

*Flowers.*—Height (Depth): About 30 to 35 mm. Diameter: About 50 to 55 mm. Petals: Arrangement: Single, sympetalous, lobed (approximately ⅓) campanulate with reflexed tips. Quantity per flower: 5. Length: 30 mm to 55 mm. Width: 10-18 mm. Tip: Acute to Slightly Cuspidate. Base: Fused on lower ⅔. Margin: Entire. Texture: Smooth. Color when opening, Upper and under surface: Base: RHS 92D, Violet-Blue. Apex: RHS 92B, Violet-Blue. Color when fully opened, Upper surface: main color RHS 88B violet with some RHS 92D violet-blue at base and around venation. More than ½ is RHS 88B violet. Color when fully opened, Under surface: RHSN88B, violet. Fading: No fading.

*Sepals.*—Arrangement: Basally fused. Appearance: Glaucescent. Quantity per flower: 5. Length: 20 to 30 mm. Width: 10 to 12 mm. Overall shape: Deltoid to Lanceolate. Tip: Acute. Base: Fused. Margin: Entire, sometimes with few teeth. Color, upper and under surfaces: Between RHS 146A and 147B, yellow-green.

*Pedicels.*—Angle: 20-40°. Length: 5 to 10 mm. Diameter: 2 to 3 mm. Strength: Strong. Color: RHS 137D, green, as stem.

Reproductive organs:

*Androecium.*—Stamen: Quantity: 5, fused until pollen has been shed. Anther: Shape: Almost rectangular, curling after shedding. Length: 10 mm. Color: Yellow, RHS 2D. Pollen: Amount: Very much. Color: Yellow-Orange, RHS 14D.

*Gynoecium.*—Pistil: Quantity: 1. Length: Up to 35 mm. Stigma: Shape: Tripartite and curled backwards. Color: Yellow, RHS 2D. Style: Length: About 20-25 mm. Color: Yellow, RHS 2D. Ovary: Color: RHS 137D, green, as pedicel.

Seed/fruit: None observed.

Weather tolerance: Not tested.

Disease/pest resistance: Not tested.

Disease/pest susceptibility: Not tested.

I claim:

1. A new and distinct cultivar of *Campanula* plant named 'PKMFORMA04', as illustrated and described herein.

* * * * *